(12) United States Patent
Parker

(10) Patent No.: US 9,474,849 B2
(45) Date of Patent: Oct. 25, 2016

(54) APPARATUS AND METHOD FOR REDUCING INCIDENCE OF TICK BORNE INFECTIONS

(71) Applicant: John Richard Parker, West Chester, PA (US)

(72) Inventor: John Richard Parker, West Chester, PA (US)

(*) Notice: Subject to any disclaimer, the term of this patent is extended or adjusted under 35 U.S.C. 154(b) by 0 days.

(21) Appl. No.: 14/298,334

(22) Filed: Jun. 6, 2014

(65) Prior Publication Data

US 2014/0364829 A1    Dec. 11, 2014

Related U.S. Application Data

(60) Provisional application No. 61/832,531, filed on Jun. 7, 2013, provisional application No. 61/857,234, filed on Jul. 22, 2013, provisional application No. 61/878,530, filed on Sep. 16, 2013.

(51) Int. Cl.
   *A61M 3/02* (2006.01)
   *A61B 17/50* (2006.01)

(52) U.S. Cl.
   CPC ......... *A61M 3/0237* (2013.01); *A61M 3/0262* (2013.01); *A61B 2017/505* (2013.01); *A61M 2202/20* (2013.01)

(58) Field of Classification Search
   CPC ........... A61M 3/0237; A61M 3/0262; A61M 2202/20; A61B 17/50; A61B 2017/505
   USPC .............................. 606/131; 604/294, 300, 68
   See application file for complete search history.

(56) References Cited

U.S. PATENT DOCUMENTS

| | | | | |
|---|---|---|---|---|
| 3,507,274 A | * | 4/1970 | Soichet | A61F 6/144 128/840 |
| 3,934,590 A | * | 1/1976 | Campagna et al. | 604/302 |
| 4,085,750 A | * | 4/1978 | Bosshold | A61F 9/0026 604/302 |
| 4,213,460 A | * | 7/1980 | Weiner | 606/131 |
| 4,373,526 A | * | 2/1983 | Kling | 604/117 |
| 4,543,096 A | * | 9/1985 | Keene | 604/300 |
| 4,767,416 A | * | 8/1988 | Wolf | A61M 35/003 128/200.14 |
| 5,064,420 A | * | 11/1991 | Clarke et al. | 604/295 |
| 5,170,779 A | * | 12/1992 | Ginsberg | A61F 11/006 601/161 |
| 5,221,027 A | * | 6/1993 | Gibilsco | 222/420 |
| 5,374,274 A | * | 12/1994 | Sproviero et al. | 606/131 |
| 6,004,286 A | * | 12/1999 | Bellhouse et al. | 604/68 |
| 6,332,875 B2 | * | 12/2001 | Inkpen et al. | 604/181 |
| 6,537,242 B1 | * | 3/2003 | Palmer | 604/22 |
| 8,002,757 B1 | * | 8/2011 | Schultz | A61M 3/0262 604/268 |

OTHER PUBLICATIONS

Caring for Your Baby and Young Child, p. 681, latest copyright date: 2004.*

\* cited by examiner

*Primary Examiner* — Manuel Mendez
(74) *Attorney, Agent, or Firm* — Laurence Weinberger

(57) ABSTRACT

A device and method for treating a tick bite or other skin wound that may have been exposed to pathogens employs a syringe filled with antipathogen solution whereby the solution is applied under mild pressure directly to the wound site. The device employs spreader/retractor arms to open the wound for better access of the solution into the wound. The method of using the device to cleanse and disinfect a wound is described.

9 Claims, 4 Drawing Sheets

APPARATUS AND METHOD FOR REDUCING INCIDENCE OF TICK BORNE INFECTIONS

This application hereby claims the benefit of U.S. Provisional Applications No. 61/832,531 filed Jun. 7, 2013, No. 61/857,234 filed Jul. 22, 2013, and No. 61/878,530 filed Sep. 16, 2013.

BACKGROUND OF THE INVENTION

1. Field of the Invention

Diseases resulting from tick bites are becoming epidemic. Deer tick bites, in particular, have been implicated in the spread of Lyme disease, and efficient methods of dealing with the bites are disclosed. Prompt removal of the tick and treatment with a bactericide may help prevent subsequent infections.

2. Description of Problem and Prior Art

Ticks are known to carry and transmit several diseases including Rocky Mountain Spotted Fever and Lyme disease. The prevalence of these tick borne diseases, particularly Lyme disease, has recently reached epidemic proportions in parts of the United States. It has been determined that it takes time after the initial tick bite for the pathogen to transfer from a tick into and through skin. Accordingly, prompt removal of a tick after it is noticed provides a first line of defense against infection.

Removal of a tick without causing it to inject the pathogen turns out to be very difficult. Recommendations of various sources regarding the necessity and removal of ticks are summarized in Appendix "A". The information emphasizes that during the difficult removal process, the individual should not damage, irritate, agitate, puncture, crush, squeeze or break the tick. If one or more of these unfortunate occurrences should happen, the pathogen in the saliva glands in the forward portion or further back in the body of the tick can be expelled deep into the wound. Doctors state that it is extremely difficult to remove an imbedded tick, particularly a very small deer tick, without causing one or more of the above listed items to occur. This is the case since ticks have a barbed hypostome that anchors the tick in the skin. With just a washing of the general area, it is clearly very difficult to kill the pathogen in the depth of a bite wound in which a tick has also deposited salivary cement on walls of the wound. The pathogen bonds to the tick's saliva protein (known as SALP 15 protein) as a cloaking device As a result, a very large number of people may now have Lyme disease or other tick borne diseases because they only used soap and water or alcohol to wash off the general area of the bite.

An approach is needed that will kill the pathogen deep in the wound and quickly separate the SALP 15 protein and pathogen from the wound and immediate area. In the case of Lyme disease, for example, because the deer tick does not expel the pathogen for many hours after it has embedded and then many times expels on removal, such an approach provides the opportunity to kill pathogens at the wound site before they get into the blood circulatory system.

DETAILED DESCRIPTION OF THE INVENTION

Definitions

Figure 1:
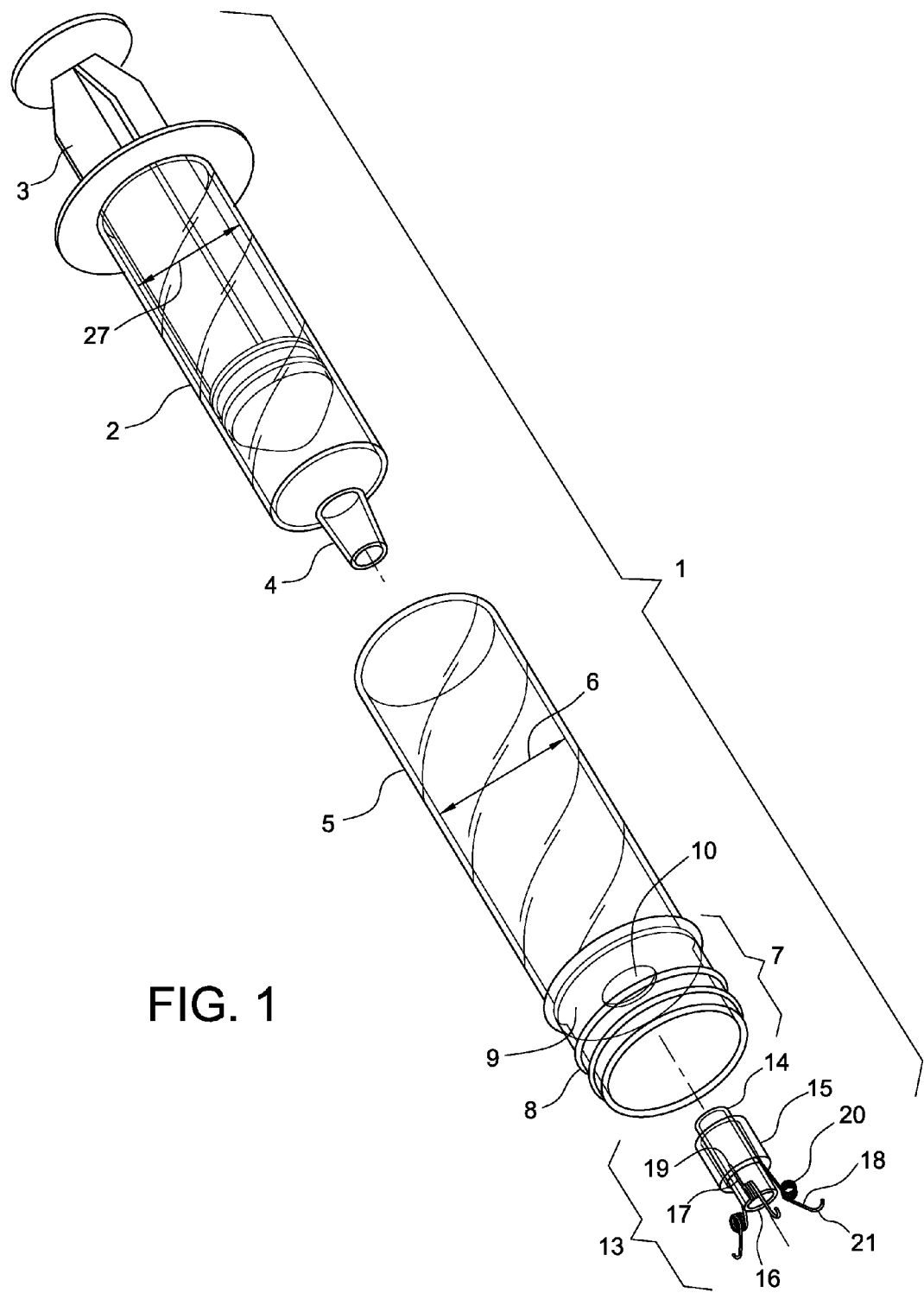
FIG. 1 shows a partially exploded view of the interceptor.

In the following description of the invention, DISTAL refers to the end of the device or its parts that will be closest to the site of application against skin during use.

In the following description of the invention, ANTERIOR refers to the end of the device or its parts that will be furthest from the site of application against skin during use.

Description:

The present invention provides an interceptor device and method by which pathogens deposited by tick wound or other types of small wounds may be killed or significantly reduced in number before having an opportunity to enter the blood stream.

In the figures like numbers denote the same part. With reference to the Figures, the interceptor device 1 of the invention comprises of a flushing needleless syringe 2 with plunger 3 which has an elongated dispensing conical tip 4. A splash shield 5 has an inner diameter 6 larger than the outer diameter 27 of syringe 2 so that syringe 2 may pass into splash shield 5. Once assembled, splash shield 5 surrounds the discharge conical tip 4 of syringe 2. The distal end 7 of shield 5 is transparent so that the areas of contact of the device with the skin can be observed. End 7 may have guide rings 8. Shield 5 has a retaining ring 9 located near its distal end 7. Retaining ring 9 has a centrally located circular opening 10.

A spreading and delivery assembly 13 attaches to conical tip 4. Spreading and delivery assembly 13 consists in part of two concentrically mounted tubes 14 and 15. The outside diameter of tube 14 approximates the interior diameter of tube 15. Tube 14 extends beyond the distal end of tube 15 and forms a discharge port or nozzle 16. The anterior end of tube 14 extends beyond the anterior end of tube 15 then through opening 10 of retaining ring 9 of shield 5 and couples the spreading and delivery assembly 13 by compressively mounting at 22 onto conical tip 4 of syringe 2. The exterior of tube 15 fixedly engages the opening 10 in retaining ring 9.

The anterior ends 17 of several stiff but flexible spreader arms 18 are captured and firmly held in place at 19 between the outer surface of tube 14 and the inner surface of tube 15 at the distal end of tube 15. Spreader arms 18 extend distally below the distal ends of tubes 14 and 15 and further consist of spring coils 20 located approximately about half the length of the spreader arms 18. The distal ends of spreader arms 18 are rounded to form contact surfaces 21. When mounted to conical tip 4, the spreader and delivery assembly 13 extends the distal end of tube 14 and spreader arms 18 below the distal end 7 of splash shield 5. A fill tube 28 having an interior diameter slightly greater that the exterior diameter of tube 14 may be temporarily placed onto nozzle 16. A wound or a tick bite is schematically shown at 23 on the skin surface 24.

The interceptor device of this invention is intended to be used with an appropriate antipathogen or antimicrobial. Exemplary antipathogens for use against tick borne pathogens include alcohol and possibly chlorhexidine.

Method of Use:

The following steps outline the general overall procedure for proper use of the interceptor device.

1) Before attempting to remove a tick, prepare the interceptor. The syringe 2 may be filled by placing the spreading and delivery assembly 13 sufficiently below the surface of an antipathogen solution so that withdrawal of the syringe plunger 3 draws antipathogen solution up into the syringe. Alternatively, a filling tube 28 may be placed onto nozzle 16 through which to draw antipathogen solution into the syringe. Set the interceptor aside.

2) After finding the tick which is embedded in the skin (or other applicable shallow insect bite wounds), using a pen or similar device mark the wound location with a small circle (about ¼" in diameter). This allows better visualization of the bite and more accurate centering. Since the tick can expel pathogen for the first time during removal, be careful to remove the tick as described at The Centers for Disease Control web site.

Figure 2:
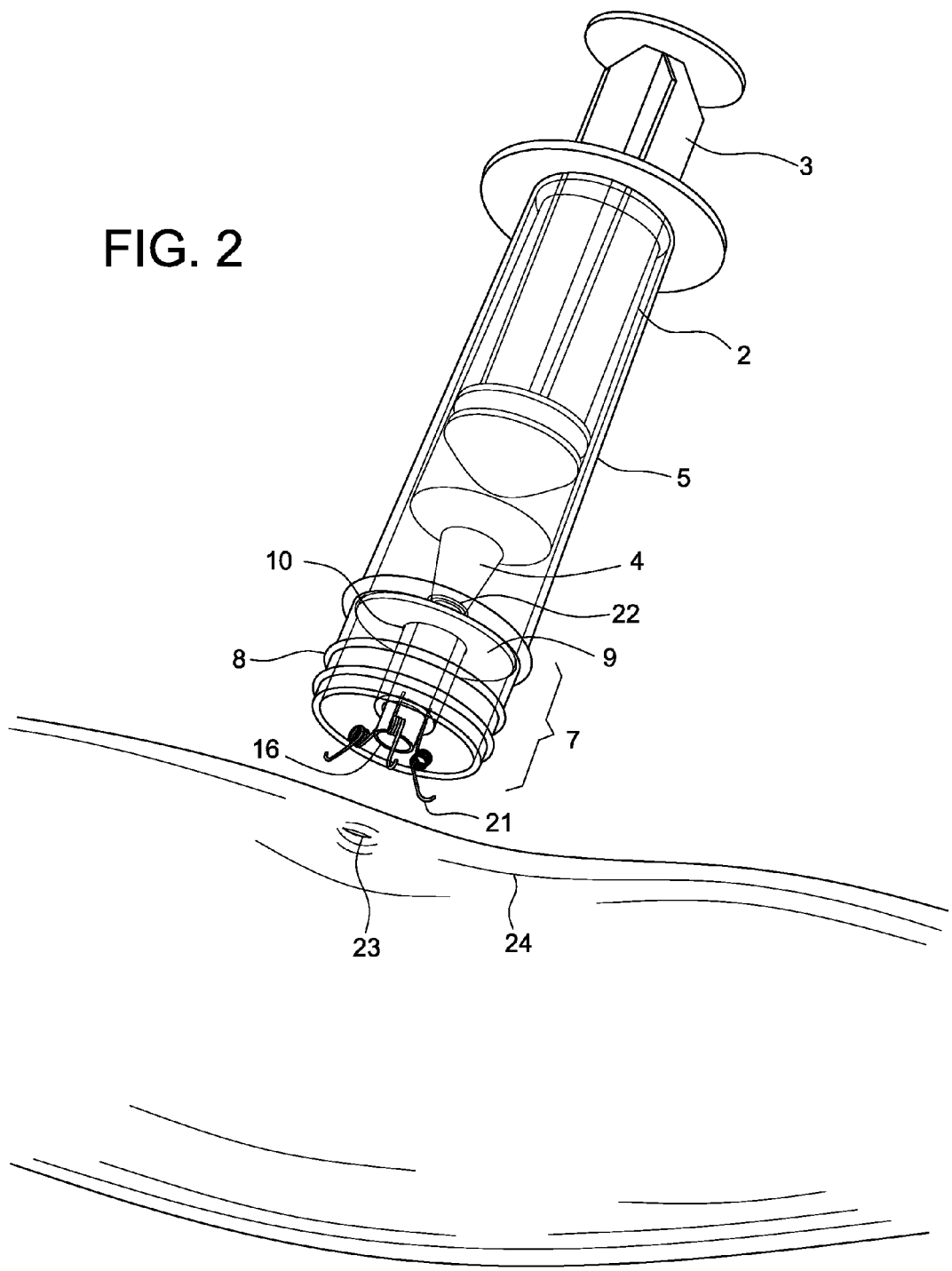
FIG. 2 shows the interceptor as it is moved towards the skin surface.
Figure 3:
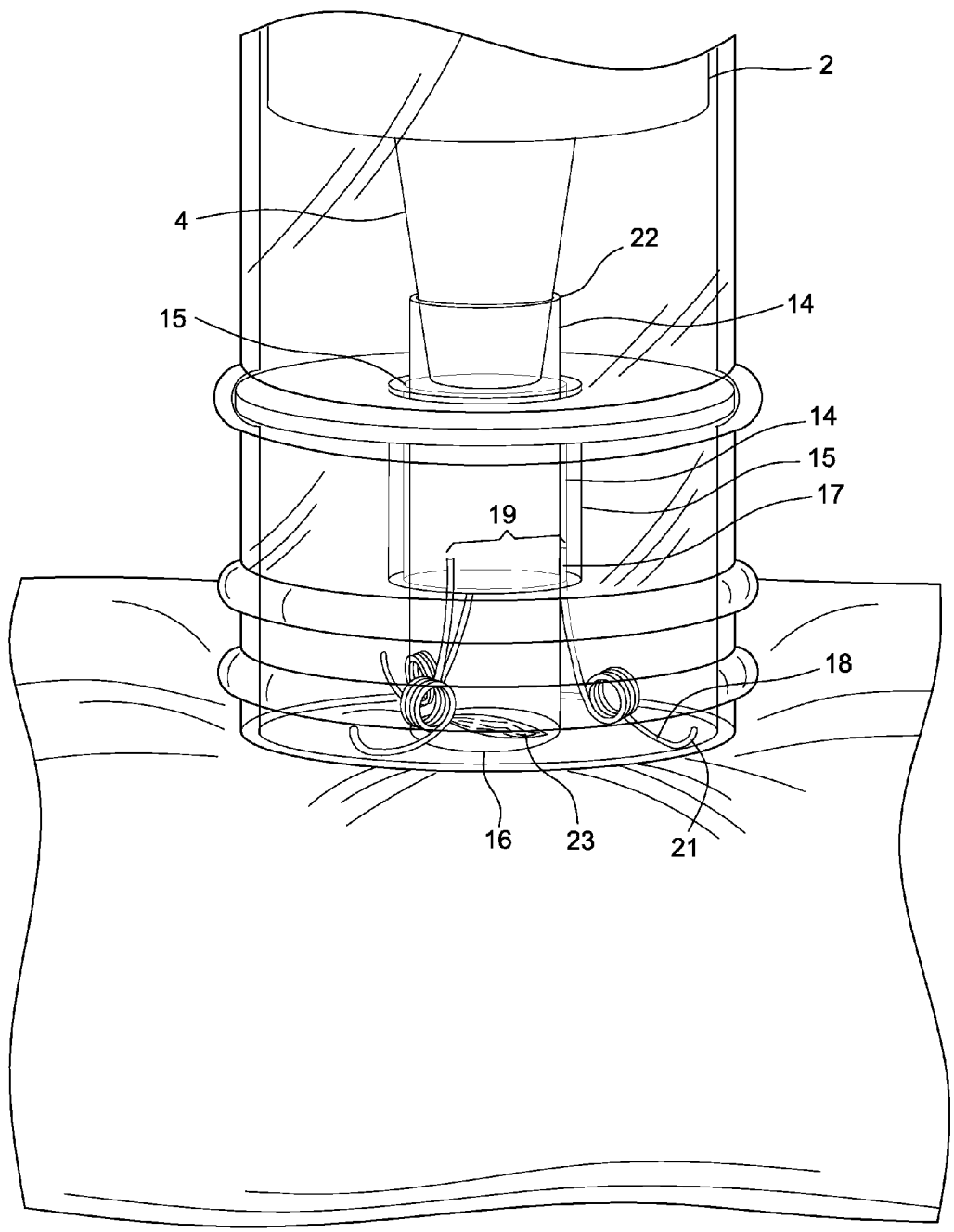
FIG. 3 shows the nozzle of the interceptor firmly pressed against the skin over a wound, the spreader arms engaging and tensioning the skin around the wound, and the splash shield engaging the surface of the skin.

3) Disinfect the wound area with rubbing alcohol or other antipathogen recommended for use on Lyme disease pathogens 4) Immediately move the interceptor 1 slowly towards the wound 23 in skin surface 24 as shown in FIG. 2 centering nozzle 16 as well as possible on wound 23. The interceptor should be applied substantially perpendicularly to skin surface 24 so that all the spreader arms 18 contact the skin at the same time. As the contact surfaces 21 of the spreader arms 18 engage the skin, they simultaneously apply pressure to tighten the skin in the immediate area of the wound in a direction outward from the wound center. The coils 20 in spreader arms 18 permit flexible movement of the spreader arms as contact with the skin is made. Continue moving the interceptor until nozzle 16 contacts and is pressed firmly against the skin around wound 23 and the splash shield 5 contacts the skin surface as shown in FIG. 3.

5) Thoroughly flush the wound multiple times by advancing the syringe piston 3 to force the alcohol or other antipathogen solution into and around the wound. Splash shield 5 protects the user from direct spray. For each flush, keep nozzle 16 pressed against the skin 24 and maintain the solution pressure generated by the syringe on the wound for several seconds in a constant manner. It is suggested that a minimum of three flushes be used with a duration of at least 5 seconds each.

6) After the last flush, leave nozzle 16 in contact with skin 24 and partially withdraw syringe piston 3 to apply suction to the wound to evacuate the contaminated fluids in the wound.

7) Empty the syringe by following standard household procedures for infectious liquids.

8) Attach the fill tube 28 to nozzle 16 and fill syringe 2 with clorhexidine by withdrawing the syringe plunger 3. Follow previous instructions for steps 4 through 6 above, but do not evacuate after the last flush.

9) Dispose of all leftover liquids, devices and materials in a safe manner for contaminated products. Disinfect your hands, gloves and equipment before and after the procedure.

Special Note: The treatment procedure outlined above should be done immediately (preferably 10 to 15 sec.) after the tick is removed. Every second counts to keep the pathogen out of the blood circulatory system and possibly prevent primary and secondary infections as well. A deer tick usually does not expel the pathogen (*Borrelia spirochete*) until after the tick has been embedded for several hours (refer to the CDC website); that is why it is critical to routinely examine the skin for tick attachments. Once the pathogen has entered the blood stream, the interceptor will no longer be useful to prevent or disinfect for tick borne disease. It is recommended that a doctor be seen immediately after use of the interceptor for follow up treatment.

As the interceptor is applied to the wound area, the ends 21 of spreader arms 18 contact the skin 24 first and then spread outwards from wound 23 pulling the skin around wound 23 slightly taut thereby tightening or retracting the skin away from the wound. In the figures of this patent document, three such spreader arms 18 are shown. However, in alternative embodiments a greater or lesser number of spreader arms 18 may be used. The important feature is that the spreader arms result in forming and positioning the wound opening to permit more efficient irrigation and better accessibility. At the same time, this tightening in a direction away from the center of the wound allows small cracks and crevices to open in the skin in the immediate area of the wound within the splash guard perimeter so that the antipathogen solution can enter. Using an antipathogen such as chlorhexidine in the last flush leaves some of the fluid in the wound and surrounding area to possibly continue killing any residual pathogens.

Using the interceptor as described not only treats just the wound opening but also the entire area within the splash guard area which experiences the highest count of pathogens. This specific process aids to continually, over a period of time, kill pathogens that can gradually escape from tubular mouthparts of the tick that often break off in the wound and are not immediately retrieved during the tick removal process. Sometimes these deeply imbedded mouthparts are never retrieved.

Preferably, the distal end 7 of the splash shield 5 is transparent so the user can see the wound and guide the interceptor to exactly center nozzle 16 on wound 23 in order to topically flush, irrigate and evacuate the wound. Guide rings 8 help the user to visualize the placement of the nozzle 16 onto wound 23. The splash guard 5 may be stored in a refrigerator to cool its distal end 7 that makes contact with the skin. Use of a cool splash guard may cool the skin in the immediate area of the wound to slow blood circulation in the immediate exposed capillaries to help contain the pathogen. This may contribute to a higher kill count of infection.

Figure 4:
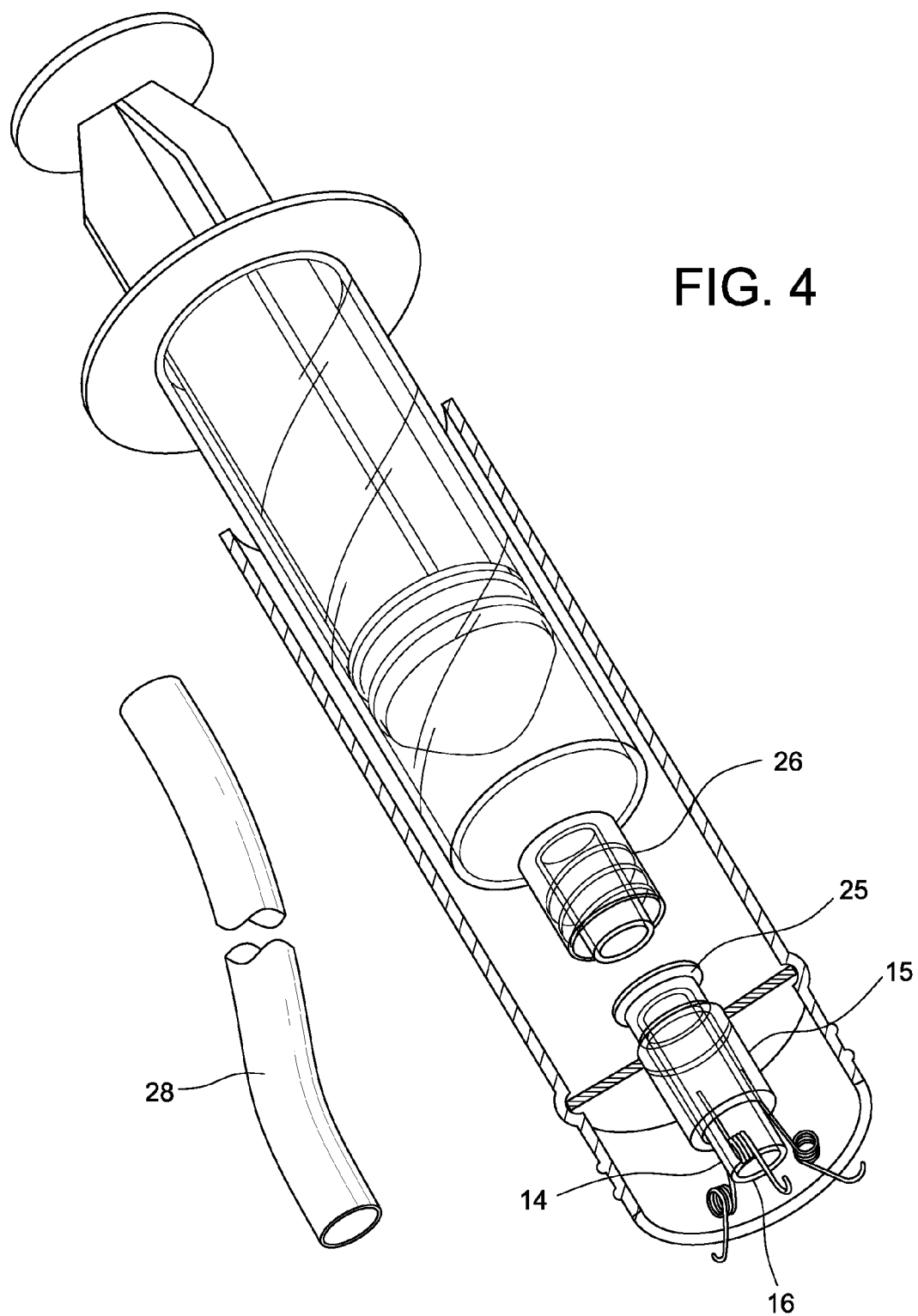
FIG. 4 shows an alternative embodiment of the spreader and delivery assembly incorporating a luer lock fitting.

In an alternative embodiment shown in FIG. 4, the spreader and delivery assembly 13 has a female luer lock 25 fastened at the anterior end of tube 14. The female luer lock 25 engages the male luer lock 26 of syringes that terminate with a male luer fitting thus permitting the spreader and delivery assembly 13 to be attached to and used with such syringes. Additionally, in yet another alternative embodiment, the nozzle 16 may be generally oval shaped in order to better approximate the shape of a wound.

The interceptor and method of the present invention provides a more thorough accessibility to the disease carrying organisms hidden in the hypostome salivary cement and the protein enhanced residuals that line the walls and the base of the wound. In the case of tick borne diseases like Lyme disease and Rocky Mountain spotted fever, these residuals add to the difficulty of making direct contact with the organisms. Use of the interceptor and the method may be applicable to other shallow insect wounds like spider bites as well as other small wounds not necessarily resulting from an insect bite. Alcohol in general has the capability to break down, denature and dilute proteins. In addition, the use of the interceptor and method of this invention could have a very significant impact on secondary infections.

Use of the interceptor is an alternative to traditional topical washing methods. The spreader arms and the nozzle of the interceptor are intended to overcome the natural inclination of the wound to close against the hypostome and protein salivary cement that impedes penetration of the antipathogen by increasing access of the antipathogen solution to the wound base and surrounding pores and crevices.

Those skilled in the art will appreciate that various modifications and alterations may be made to the device and method described in this patent document and such are considered to fall within the scope of this disclosure and appended claims.

APPENDIX "A"

The following are brief synopses of sources of tick related information:

Los Angeles County West Vector and Vector-Borne Disease Control

Do not twist or jerk the tick; this may cause mouthparts to break off and remain in the skin. Remove these with tweezers or infections may occur. Also, do not squeeze, crush or puncture the body of the tick. Its fluids (saliva, hemolymph, gut contents) may contain infectious organisms. Do not handle the tick with bare hands because infectious agents may enter through mucous membranes or breaks in the skin.

U.S. Army Center for Health

Ticks secrete a cement-like substance during feeding, securing the mouthpart (hypostome) to your wound wall, adding to removal difficulty. Do not squeeze, crush or agitate the tick because this may force infectious body fluids through the mouthparts into the wound. A secondary infection can occur.

Harvard Medical School

Improper removal methods can cause the tick to deposit more of its disease carrying secretions into the wound which increases the risk of infection. Try not to crush or squeeze the tick during the removal process. The tick deposits salivary cement into the wound.

Patient Information (Sources: Linden Hu, M.D., Allen C. Steere, M.D., Jennifer Mitty, M.D.)

Improper removal may cause the tick to act as a syringe, thereby injecting bodily fluids in the wound. Do not squeeze, crush or puncture the tick as the body fluids may contain infectious organisms.

Lymedisease.org

Broken off mouthparts can cause secondary infections so it is best to try to remove them. Do not squeeze or crush the body of the tick; this may force infected body fluids through the mouthparts into the wound. Do not agitate the tick by removal with liquids or heat.

MedicineNet.com (Source: William C. Shiel Jr., M.D. FACP, FACR)

Wear gloves; don't spread pathogens from the tick. Breaking of the tick increases the chance of infection. Crushing of the tick may release pathogens. Improper removal can cause the tick to release fluids into the wound, increasing the chances of transmitting disease. If the mouthparts and head remain in the wound, have them removed by a doctor.

Patient Information: Beyond the Basics (Sources: Linden Hu, M.D., Jennifer Mitty, M.D., MPH, Allen C. Steere, M.D.)

Improper removal may cause the tick to behave like a syringe, injecting into the wound. Do not squeeze, crush or puncture the body of the tick, since its body fluids may contain infectious organisms.

Managing Lyme Disease, 16th Edition, October, 2008, Page 36 (Patient Instructions)

Remove the tick; then apply antiseptic. Do not irritate them with heat or chemicals or grasp the body, as this may cause the tick to inject germs. Prophylactic antibiotic treatment is highly recommended if the tick was improperly removed. If the tick's contents made contact with the wound from the tick being squeezed, an infection could occur.

Centers for Disease Control

Use a set of fine-tipped tweezers to remove the tick. Don't twist or jerk the tick; this can cause mouthparts to break off. If this happens remove the mouthparts with tweezers. Thoroughly clean the bite area and your hands with rubbing alcohol.

I claim:

1. An apparatus for retracting and flushing skin wounds comprising:

a) a syringe having a projecting extension at its delivery end through which fluid may be drawn into and expelled from the syringe; and b) a retraction and fluid delivery assembly further comprising:

i) a fluid delivery tube having at a first end a means for attaching the tube to the syringe projecting extension and having at a second end a nozzle; and ii) at least two stiff but flexible spreader arms fixedly attached at the nozzle end of the delivery tube and disposed about the tube in positions determined by 360 degrees divided by the number of spreader arms, the spreader arms extending beyond the nozzle end of the delivery tube; and iii) spring coils located approximately about half the length of each spreader arm wherein the spreader arms and coils flexibly apply pressure to the skin surface to tighten the skin in the immediate area of the wound in a direction outward from the wound center.

2. The apparatus of claim 1 in which the projecting extension of the syringe is a conical tip.

3. The apparatus of claim 2 in which slidable engagement provides the means for attaching the tube to the conical tip.

4. The apparatus of claim 1 is which the projecting extension of the syringe is a male luer lock.

5. The apparatus of claim 4 in which the means for attaching the tube to the projecting extension is a female luer lock.

6. The apparatus of claim 1 in which the ends of the spreader arms are rounded to form contact surfaces.

7. The apparatus of claim 1 having an outer splash shield encasing the syringe so that the nozzle extends below the distal end of the splash shield.

8. An apparatus for retracting skin wounds comprising:

a) a support;

b) at least two stiff but flexible spreader arms fixedly attached at one of their ends to the support and disposed about the support in positions determined by 360 degrees divided by the number of spreader arms, the spreader arms extending beyond the end of the central support; and c) spring coils located approximately about half the length of each spreader arm wherein the spreader arms and coils flexibly apply pressure to the skin surface to tighten the skin in the immediate area of the wound in a direction outward from the wound center.

9. The apparatus of claim 8 in which the ends of the flexible spreader arms are rounded to form contact surfaces.

* * * * *